(12) United States Patent
Thompson et al.

(10) Patent No.: US 7,491,545 B2
(45) Date of Patent: Feb. 17, 2009

(54) EXCITATION RATIOMETRIC FLUOROSCENT BIOSENSOR FOR ZINC ION AT PICOMOLAR LEVELS

(76) Inventors: Richard Thompson, 7106 Bristol Rd., Baltimore, MD (US) 21212; Michele Cramer, 6 Britow Ct., Baltimore, MD (US) 21234; Carol Ann Fierke, 5001 Birkdale Dr., Ann Harbor, MI (US) 48103; Hui Hui Zeng, 12245 Heathcliff Ct., Ellicott City, MD (US) 21042; Rebecca Bozym, 230 Glen More Dr., Moon Township, PA (US) 15108

( * ) Notice: Subject to any disclaimer, the term of this patent is extended or adjusted under 35 U.S.C. 154(b) by 874 days.

(21) Appl. No.: 10/673,409

(22) Filed: Sep. 30, 2003

(65) Prior Publication Data

US 2004/0185518 A1   Sep. 23, 2004

Related U.S. Application Data

(60) Provisional application No. 60/416,515, filed on Oct. 8, 2002, provisional application No. 60/414,657, filed on Oct. 1, 2002.

(51) Int. Cl.
    *G01N 33/20* (2006.01)
(52) U.S. Cl. .............. 436/81; 435/15; 435/18; 436/73; 436/74; 436/166; 436/172
(58) Field of Classification Search .............. 435/15, 435/18; 436/73–74, 81, 166, 172
    See application file for complete search history.

(56) References Cited

U.S. PATENT DOCUMENTS

5,439,797 A * 8/1995 Tsien et al. ................ 435/7.21
5,952,236 A * 9/1999 Thompson et al. ............ 436/77
6,130,101 A * 10/2000 Mao et al. .................... 436/546

FOREIGN PATENT DOCUMENTS

WO            00/17650       * 3/2000

OTHER PUBLICATIONS

Chen. R. F. et al, Journal of Biological Chemistry 1967, 242, 5812-5823.*
Ekins R. P. et al, Clinical Chemistry 1991, 37, 1955-1967.*
Thompson, R. B. et al, Analytical Chemistry 1993, 65, 730-734.*
Elbaum, D. et al. Journal of the American Chemical Society 1996, 118, 8381-8387.*

(Continued)

*Primary Examiner*—Arlen Soderquist
(74) *Attorney, Agent, or Firm*—Birch, Stewart, Kolasch & Birch, LLP

(57) ABSTRACT

A highly selective and sensitive of a carbonic anhydrase-based method for measurement of zinc ion by an excitation ratiometric format based on resonance energy transfer: i.e., where the zinc ion level is transduced as the ratio of fluorescence intensities excited at two different excitation wavelengths, is provided. The method can be used very well in a fluorescence microscopy format. A detection limit of about 10 pM in zinc buffered systems, a ten to one thousand-fold improvement on the Fura indicators (which respond to Ca and Mg as well), and a one hundred thousand-fold improvement on the recently described FuraZin-1 is achieved.

14 Claims, 9 Drawing Sheets

OTHER PUBLICATIONS

Koike, T. et al, Journal of the American Chemical Society 1996, 118, 12696-12703.*
Thompson, R. B. et al, SPIE 1999, 3602, 85-92.*
Thompson, R. B. et al, SPIE 1999, 3603, 14-22.*
Thompson, R. B. et al, SPIE 1999, 3858, 161-166.*
Boisclair, M. D. et al, Journal of Biomolecular Screening 2000, 5, 319-328.*
Jensen, K. K. et al, Biochemistry 2001, 40, 938-945.*
Thompson, R. B. et al, SPIE 2001, 4255, 88-93.*
Hammarstrom, P. et al, Journal of Biological Chemistry 2001, 276, 21765-21775.*
Thompson, R. B. et al, Journal of Biomedical Optics 2002, 7, 555-560.*
Tyagi, S. et al, Nature Biotechnology 2000. 18, 1191-1196.*
Imamoto, Y. et al, Biochemistry 2000, 39, 15225-15233.*

* cited by examiner

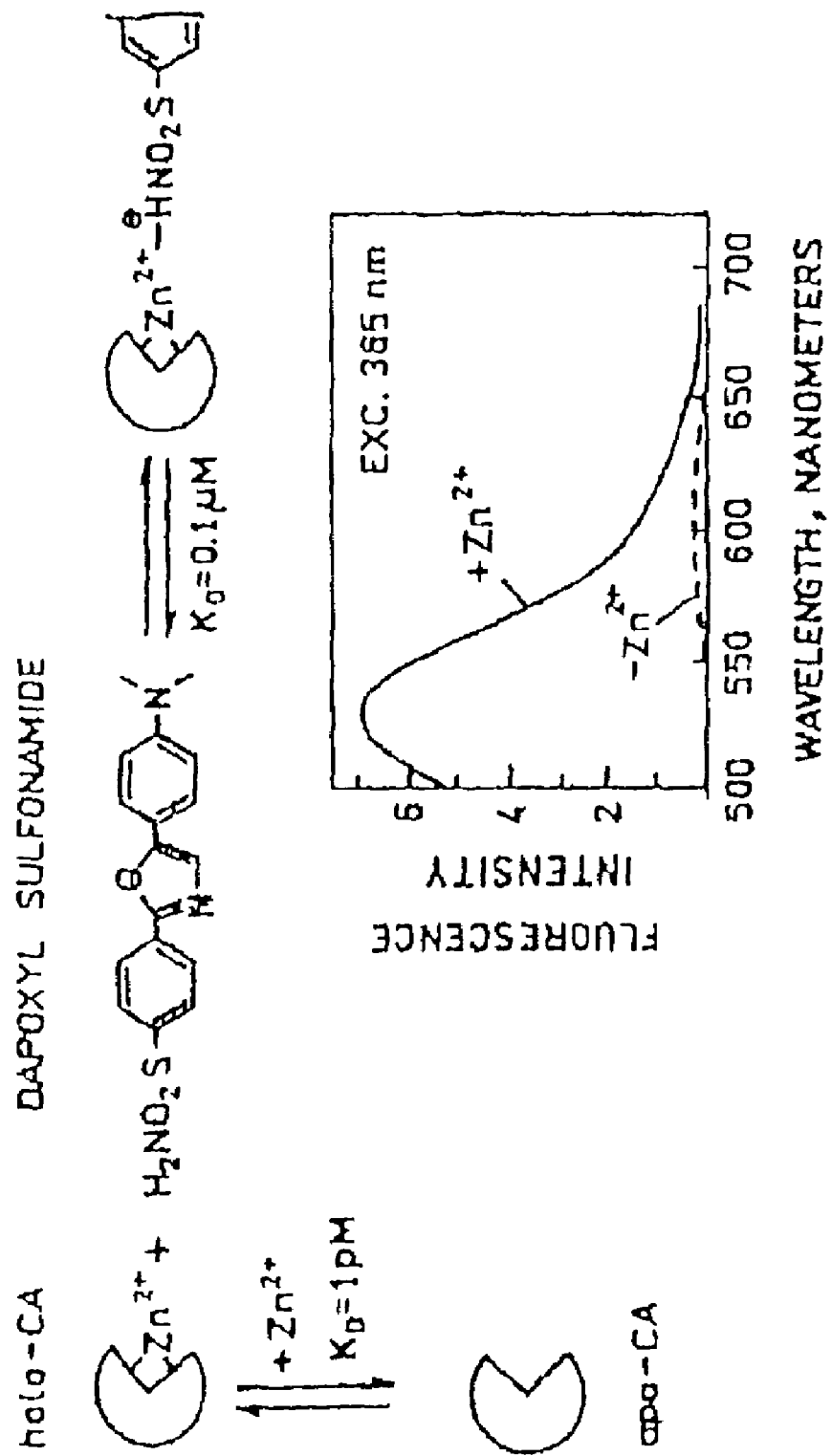
Fig. 1 Schematic of Zn(II) determination by fluorescence using apocarbonic anhydrase and Dapoxyl sulfonamide.

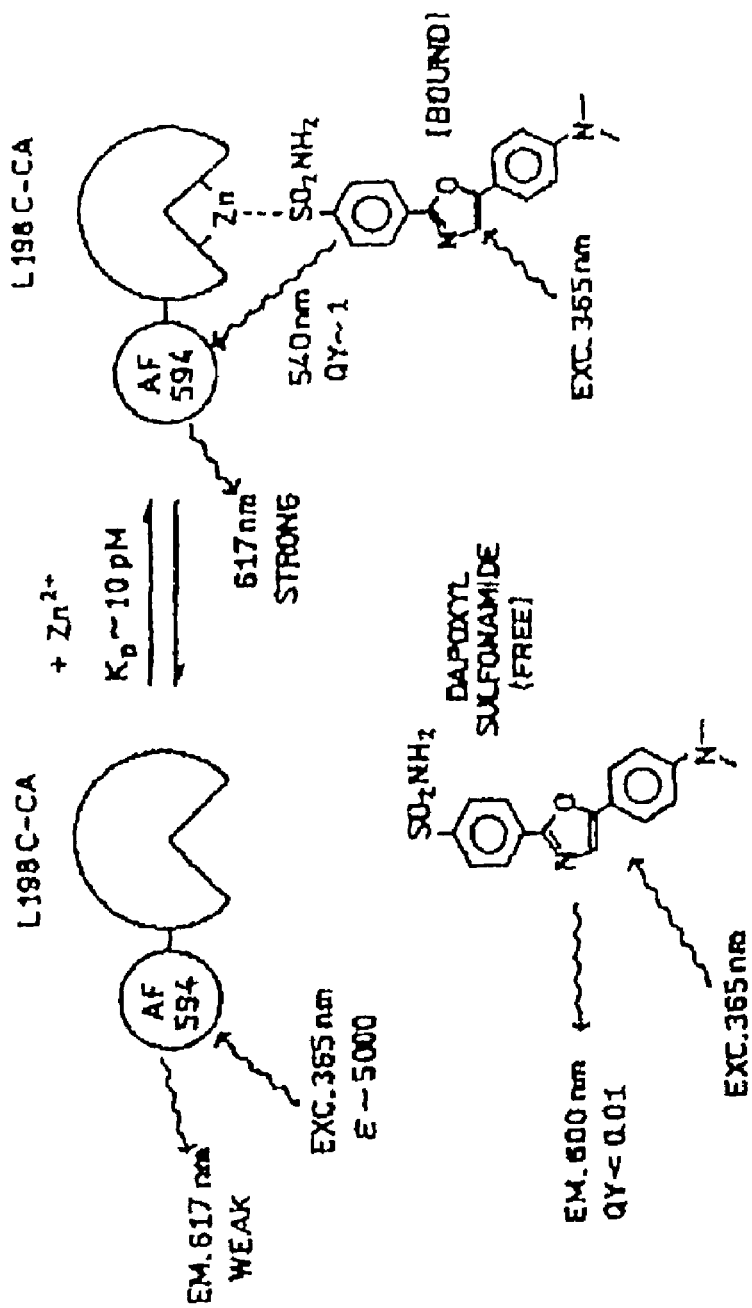
Fig. 2 Schematic of ratiometric determination of Zn(II) with apoL198C-Alexa Fluor 594 carbonic anhydrase and Dapoxyl sulfonamide.

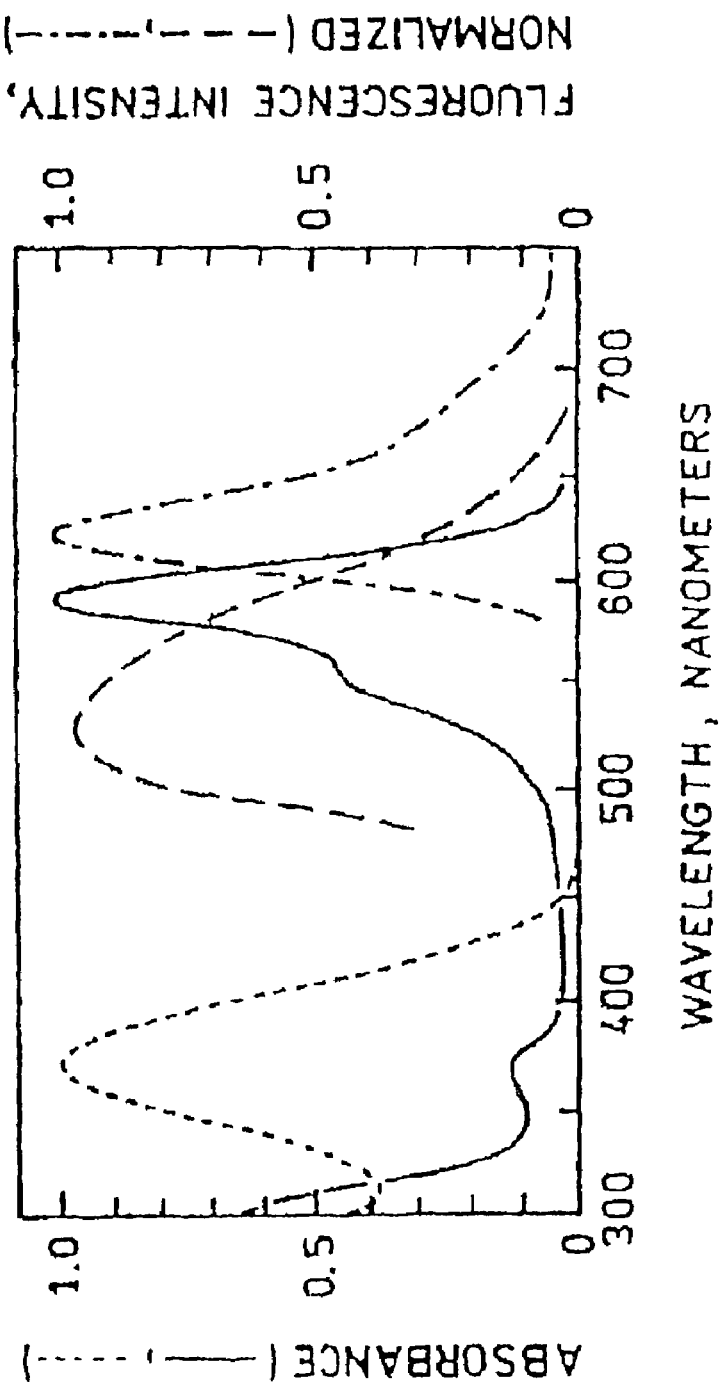
Fig. 3 Absorbance (——) and emission (– – –) spectra of apoL198C-Alexa Fluor 594 apocarbonic anhydrase, together with absorbance (- - -) and emission (-·-·-) spectra of Dapoxyl sulfonamide bound to holo carbonic anhydrase.

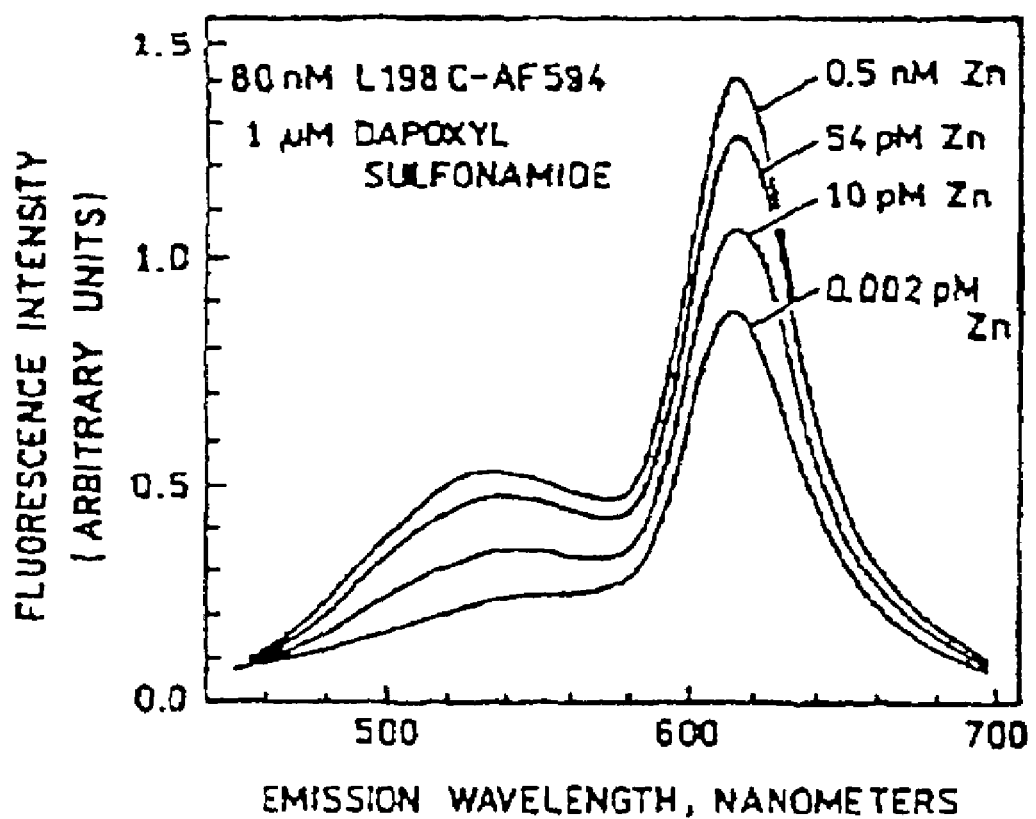
Fig. 4 Emission spectra of 80 nM apoL198C-Alexa Fluor 594 and 1 μM Dapoxyl sulfonamide in the presence of solutions buffered at (in ascending order at 610 nm) 0.002, 10, 54, and 0.5 nM free Zn(II); excitation at 365 nm.

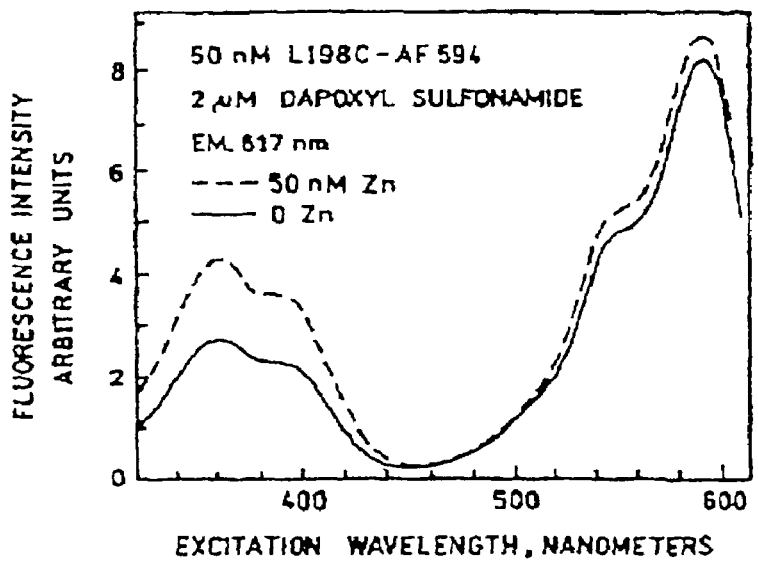
Fig. 5 Excitation spectra of 50 nM apoL198C-Alexa Fluor 594 and 2 μM Dapoxyl sulfonamide in the absence (—) and presence of 50 nM free Zn(II) (– –); emission at 617 nm.
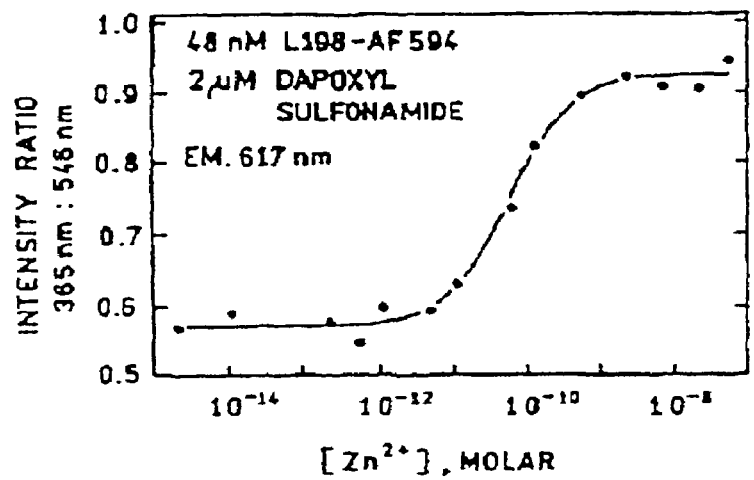
Fig. 6 Zinc-dependent ratio of emission at 617 nm excited at 365 nm to that excited at 548 nm of 48 nM apoL198C-Alexa Fluor 594 and Dapoxyl sulfonamide; the line is the best fit binding isotherm.

EXCITATION RATIOMETRIC FLUOROSCENT BIOSENSOR FOR ZINC ION AT PICOMOLAR LEVELS

This application claims priority to U.S. Provisional Application Nos. 60/414,657 filed on Oct. 1, 2002 and 60/416,515 filed Oct. 8, 2002 under 35 U.S.C. § 119(e), the contents of which are herein incorporated by reference.

FIELD OF THE INVENTION

The present invention relates to a biosensor for measurement of zinc ion in a sample. The invention provides composition and methods for measuring zinc ion at picomolar concentrations in vitro and in vivo.

BACKGROUND OF THE INVENTION

Zinc is an ion of growing importance in many field of biology and medicine. In particular, recent work has demonstrated the excitotoxic role(s) of zinc in the brain, [1-3] as well as its potential role as a signaling ion in the brain [4] which recent evidence suggests participates in long term potentiation [5]. Elsewhere in the body, zinc seems to play a role in the immune response [6], and is a prevalent constituent of semen, as well as an essential cofactor in many enzymes [7] and the ubiquitous "zinc fingers" of transcription factors [8]. The role of zinc in apoptosis is the subject of controversy [9], and there is no consensus as to how zinc is distributed in the body, allocated amongst its many role(s), or how these processes are regulated. The availability of selective, sensitive, quantifiable fluorescent calcium indicators beginning with Quin-2, Fura-2, and Indo-1 [10] has revolutionized our understanding of calcium, and if analogous indicators were available for zinc, perhaps comparable progress could be made. Despite substantial effort [9, 11-16], it is only recently that fluorescent zinc indicators have been made which offer adequate selectivity over potential interferents such as Ca and Mg; reliable quantitation through intensity ratios, anisotropy, or fluorescence lifetime; and useful sensitivity. In particular, the recently introduced FuraZin-1 and Newport Green DCF from Molecular Probes offer selectivity (Thompson, et al., *J. Neuroscience Methods* (2002), hereby incorporated by reference), micromolar sensitivity, and quantitation by excitation intensity ratio (FuraZin) and fluorescence lifetime (Newport Green).

However, substantial recent evidence suggests that, as in the case of calcium elucidation of the biology of zinc will require in many cases significantly better sensitivity than the above indicators offer. In particular, release of zinc into the ventrical of rabbit brain following transient global ischemia or blunt force trauma yields peak levels in the nanomolar range, against a background of less than five nanomolar (Frederickson, et al., in preparation). The affinity of the NR2A subunit of AMPA receptor for Zn(II) has been measured in vitro to be 20 nM[17], suggesting that it responds to zinc levels in this regime. Ordinarily the free Zn(II) concentration in serum is one nanomolar or less, based on measurements and calculations incorporating the affinities of the two principal Zn buffers, α2-macroglobulin and serum albumin [18]. Recent work suggests that free Zn(II) concentrations may be very low in bacterial cells [19]. While other recent results (Thompson, et al., submitted) [20] indicate that the stimulus-induced release of zinc in hippocampus is in the micromolar range, the lower range indicated by the above measurements suggests that it will be necessary to measure lower concentrations, particularly inside cells.

BRIEF DESCRIPTION OF THE DRAWINGS

FIG. 1. Schematic of Zn(II) determination by fluorescence using apocarbonic anhydrase and Dapoxyl sulfonamide.

FIG. 2. Schematic of ratiometric determination of Zn(II) with apoL198C-ALEXA FLUOR 594 (pyrano[3,2-g:5,6-g'] diquinolin-13-ium, 6-[2-carboxyl-4 (or 2-carboxyl-5) [ carboxamido-N-pentyl-N'-maleimide]phenyl]-1,2,10,11-tetrahydro-1,2,2,10,10,11-hexamethyl-4,8-bis(sulfomethyl); inner salt) carbonic anhydrase and Dapoxyl sulfonamide.

FIG. 3. Absorbance (—) and emission (— — —) spectra of apoL198C-ALEXA FLUOR 594 apocarbonic anhydrase, together with absorbance (————) and emission (— — —) spectra of Dapoxyl sufonamide bound to holo carbonic anhydrase.

FIG. 4. Emission spectra of 80 nM apoL198C-ALEXA FLUOR 594 and 1 μM Dapoxyl sulfonamide in the presence of solutions buffered at (in ascending order at 610 nm) 0.002 pM, 10 pM, 54 pM, and 0.5 nM free Zn(II); excitation at 365 nm.

FIG. 5. Excitation spectra of 50 nM apo L198C-ALEXA FLUOR 594 and 2 μM Dapoxyl sulfonamide in the absence (—) and presence of 50 nM free Zn(II)(— —); emission at 617 nm.

FIG. 6. Zinc-dependent ratio of emission at 617 nm excited at 365 nm to that excited at 548 nm of 48 nM apoL198C-ALEXA FLUOR 594 and Dapoxyl sulfonamide; the line is the best fit binding isotherm.

DESCRIPTION OF THE INVENTION

Figure 7:
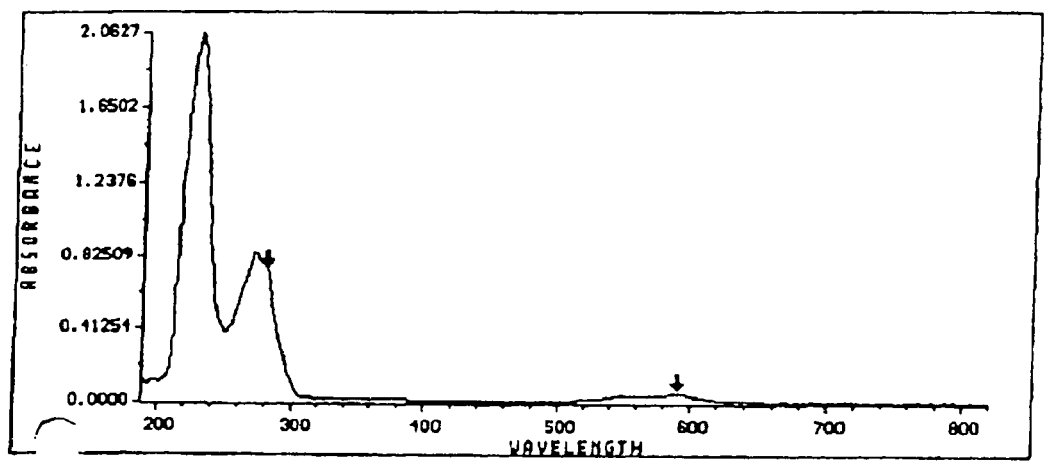
FIG. 7. UV-vis spectrum of apo-S166C-AF594 showing the poor labeling efficiency of this variant.

The present invention utilizes measurement of photoluminescence of paired fluorophores to determine the amount of zinc ion in a sample. The method employs a donor fluorophore, which reversibly binds to carbonic anhydrase (CA) in a zinc-dependent fashion. Excitation energy absorbed by the donor fluorophore is then transferred to an acceptor fluorophore that is associated with the CA protein in some fashion. A photoluminescent emission from the acceptor fluorophore is then measured. A second measurement is also made of a photoluminescent emission from the acceptor fluorophore when it is directly excited at a second wavelength, i.e., one different from that of the light used to excite the donor fluorophore. Measurement of the ratio of the photoluminescent emission from the acceptor fluorophore at the two different excitation wavelengths can be related to the concentration of zinc present in the sample.

Of the various kinds of photoluminescence, fluorescence and phosphorescence are the preferred kinds to measure in the present invention. For instance, eosin can be used as an acceptor fluorophore from which either phosphorescent or fluorescent emission is measured.

Our laboratories have developed a series of fluorescent zinc indicators based on the high affinity (1 pM) and outstanding selectivity of human apocarbonic anhydrase II (CA) [21-24]. The selectivity of CA for Zn(II) is outstanding: Ca(II) and Mg(II) do not interfere at concentrations of 10 mM and 50 mM, respectively, and other divalent cations which bind (Cu, Cd, Ni, and Co) are seldom found free above trace levels in most organisms. Moreover, these metals do not promote binding of sulfonamides and the concomitant fluorescent change, so they do not create a false positive response, but do affect quantitation. In measurements in organotypic cell cultures [25], hippocampal slices [26], and extracellular fluid (Thompson, et al., submitted; Frederickson, et al., in preparation), the interference is evidently quite small. Most CA-based Zn determinations take advantage of the propensity of the holo-form of CA to bind aryl sulfonamides in the anionic form as a fourth ligand to the active-site Zn(II), replacing the water molecule usually found there [27]. In the absence of zinc, binding of the aryl sulfonamide is usually at least 1000-fold weaker [28]. If the aryl sulfonamide is fluorescent, binding to the protein nearly always causes a change in its fluorescence anisotropy [29], and for selected arylsulfonamides there may be changes in intensity, spectral properties, quantum yield and lifetime [25, 28, 30, 31]. The fluorescent changes of the sulfonamide can thus be related to its fractional occupancy of the binding site on the protein, which is in turn determined by the presence of zinc therein; since the zinc binding is a simple function of the free zinc concentration, the fluorescence changes can be used to determine the free zinc concentration. An example of this is Dapoxyl sulfonamide, which upon binding to the holoprotein exhibits a 60 nm blue shift of its emission, and a twenty-fold increase in its lifetime and quantum yield, permitting determination of zinc by lifetime, intensity changes, or the ratio of intensity changes at two emission wavelengths [31] (FIG. 1).

However, for quantitative analysis by fluorescence microscopy, only certain transduction modes are preferred. Intensity ratios at two different emission or excitation wavelengths, as well as anisotropy or lifetime measurements, offer facile calibration and relative freedom from artifact compared with intensity measurements. While several fluorescence lifetime microscopes have been demonstrated [32-34], and are commercially available from two manufacturers, such instruments are not yet in widespread use. Similarly, although fluorescence polarization microscopy has been demonstrated by Axelrod and Verkman [35, 36], this technique is also not in widespread use. Particularly for calcium imaging, intensity ratios have been preferred, and especially the ratio of emission intensity at two differing excitation wavelengths. This is because in the fluorescence microscope changing excitation wavelengths has little impact on the image quality, whereas changing the emission wavelength often affects the image quality. Moreover, changing the excitation wavelength can be done quickly using acousto-optic tunable filters to image rapidly changing specimens, whereas this is harder on the emission side. Currently there are a large number of fluorescence microscopes capable of excitation ratiometric measurements in use.

While some of the fluorescent aryl sulfonamides exhibit shifts in their excitation upon binding [25, 30], these shifts are too small to be useful. We developed a Forster resonance energy transfer (FRET) approach to selectively observe the binding of an arylsulfonamide as a change in intensity at two different excitation wavelengths. This is illustrated in FIG. 2. In a preferred embodiment of this invention, Dapoxyl sulfonamide is used as the zinc-dependent CA binding fluorophore.

U.S. Pat. No. 6,225,127 teaches determination of zinc by a fluorescent donor-labeled carbonic anhydrase and a colored ligand whose binding is metal-dependent and which can serve as an energy transfer acceptor for the fluorescent label; upon binding of the metal the ligand is brought within close proximity causing an increase in energy transfer efficiency and a concomitant decrease in the intensity and average lifetime of the donor. The present invention is distinguished from the invention of U.S. Pat. No. 6,225,127 because in the present invention the fluorescent label on the carbonic anhydrase is an acceptor, not a donor, the ligand is a donor, not an acceptor; and the metal ion level is preferably transduced as a ratio of intensities at two different excitation wavelengths (corresponding to the donor and acceptor excitation) observed at a single emission wavelength (that of the acceptor). Furthermore, in the present invention the fluorescence emission of the acceptor is observed, whereas in U.S. Pat. No. 6,225,127 the emission of the donor is observed, and there is no ratiometric response in the invention described in U.S. Pat. No. 6,225,127.

Other compounds exhibiting zinc dependent binding to CA and a concomitant change in fluorescence properties, and thus useful as donor fluorophores according to the present invention are described in, for example U.S. Pat. Nos. 5,545,517 and 6,197,258, hereby incorporated by reference.

Acceptor fluorophores to be paired with particular donor fluorophores can be determined by one of ordinary skill in the art by examination of overlap integrals of fluorescence and excitation spectra of candidate pairs of compounds. The necessary considerations are briefly summarized below and then exemplified by the Dapoxyl sulfonamide-ALEXA FLUOR 594 pair.

Criteria for good donor-acceptor pairs include: 1) the donor should have strong absorbance at a convenient excitation wavelength; 2) the donor should bind tightly to the protein in the holo form and much more weakly to the apo-form; 3) the donor should have a good quantum yield when bound; and 4) the donor should transfer energy efficiently to the acceptor when bound to the protein. Energy transfer efficiency is in turn primarily a function of donor proximity to the acceptor, overlap of the donor emission spectrum with the acceptor absorbance spectrum), and quantum yield of the donor, as described in the well-known theory of Forster (Forster, 1948). Several fluorescent compounds which meet these criteria are known, including dansylamide (R. F. Chen et al. (1997), Biol. Chem. 242:5813-5823), ABD-N (R. B. Thompson et al (2000), J. Neuroscience Methods 96:35-45), ABD-M (R. B. Thompson et al. (1998), Anal. Chem. 70:1749-1754), benzothiazolyl coumarin sulfonamide (BTCS), and Dapoxyl sulfonamide (R. B. Thompson et al (2000), J. Biomedical Optics 5:17-22), as well as the fluoresceinyl aryl sulfonamide of Elbaum, et al. (4-aminosulfonyl [1-(4-N-(5-fluorsceinylthioureido) butyl)]-benzamide, D. Elbaum et al (1996), J.Am. Chem. Soc. 118:8381-8387). All of these compounds are workable in the present invention, with suitably positioned and chosen acceptors (see below). All of these compounds are aryl sulfonamides which are also inhibitors of the reaction catalyzed by carbonic anhydrase. Several hundred such inhibitors of carbonic anhydrase are known to the art because of their therapeutic importance in treating glaucoma (T. H. Maren (1977), Am. J. Physiology 232:F291-F297); nearly all are sulfonamides and most are aromatic. Whether an inhibitor has fluorescence properties suitable for use in the invention can be determined by methods known in the art. For purposes of the present invention, it is immaterial that a compound inhibits the enzymatic reaction, but the compound must exhibit metal-dependent binding to CA. Most compounds which exhibit metal-dependent binding to CA are also effective inhibitors and therefore the class of compounds of CA inhibitors is a fruitful group to examine for additional embodiments of the donor fluorophore.

Aryl sulfonamide inhibitors are preferred compounds for use in the present invention because their binding to the CA is typically metal-dependent. The mechanism and structural requirements of aryl sulfonamide CA inhibitors are known, such that the affinity of a particular molecule can be predicted and inhibitors with high affinity can be designed de novo (B. A. Grzybowski (2002), Proc, Nat'l. Acad. Sci. USA 99:1270-1273). Of the group of fluorescent aryl sulfonamide inhibitors listed above, a preferred one is Dapoxyl sulfonamide, for four reasons in addition to the above criteria. First, Dapoxyl sulfonamide exhibits very little fluorescence emission when not bound to the protein, and therefore does not interfere in the measurement. Secondly, Dapoxyl sulfonamide has a large Stokes' shift, so that the acceptor can be selectively excited by a suitable (second) wavelength without exciting the donor. Third, its emission exhibits a large blue shift upon binding to holo-CA, and since the acceptor can be chosen to preferentially accept this emission as opposed to the emission from the unbound donor, the sensitivity is improved. Finally, Dapoxyl sulfonamide readily penetrates cell membranes, permitting measurements inside cells.

There are similar criteria for evaluating the suitability of a particular fluorescent label or protein moiety fused to carbonic anhydrase for use as the acceptor fluorophore, and placement of the fluorophore for this purpose. A suitable acceptor fluorophore should be chosen to have good absorbance at the emission wavelength of the donor emission (such that a large overlap integral exists with a correspondingly long Forster distance at which energy transfer is 50% efficient), high quantum yield, as high a Stokes' shift as possible, and should not interfere with the binding of the aryl sulfonamide. In general, one would choose the positioning of the acceptor and its overlap integral with the donor such that 90 or more percent of the emission energy from the donor is transferred from the bound donor to the acceptor for best sensitivity; however, a lower percentage still will work. Thus, it is acceptable that from 30 to 100 percent of the energy be transferred, more acceptable that from 50 to 100 percent of the energy be transferred and yet more acceptable that 75 to 100 percent of the energy be transferred. However, it is more typical that 70 to 90 percent of the donor emission energy is transferred. We note that this is distinct from earlier energy transfer-based assays wherein it is preferable that not more than 75% of the energy is transferred, and greater than 90% is deleterious (R. B. Thompson et al. (1996), J. Biomedical Optics 5:17-22).

Similarly, one may use conjugatable fluorophores which react with other moieties on the protein surface (such as free amines) for energy transfer-based metal ion assays if, as a result of the conjugation process they are positioned reasonably close to the donor. Thiol-conjugatable labels are preferred for use in the present invention because a cysteinyl residue can be inserted in the amino acid sequence of the CA in place of another residue such that in the rigid framework of the protein the cysteine residue is at a fixed and optimal distance from the donor; acceptors placed at longer distances will reduce sensitivity.

One acceptor fluorophore that meets these criteria for Dapoxyl sulfonamide as a donor is ALEXA FLUOR 594, but several fluorophores are known in the art that have similar spectral properties which would make them acceptable if they were positioned similarly. Thus Texas Red malemide (Molecular Probes T-6009) and tetramethyl rhodamine maleimide (Molecular Probes T-6027) have similar spectral properties to ALEXA FLUOR 594, and would respond to zinc (in the presence of, e.g., Dapoxyl sulfonamide) if attached to a suitable cysteinyl residue on the carbonic anhydrase surface. Other fluorescent labeling molecules may be used with other fluorescent aryl sulfonamides. Examples of such thiol-conjugatable probes (with Molecular Probes catalog number) together with suitable fluorescent aryl sulfonamides listed above would include:

| Aryl sulfonamide | Thiol-conjugatable fluorescent acceptor |
| --- | --- |
| dansylamide | Lucifer Yellow iodoacetamide (cat. no. L-1338) |
| | PyMPO epoxide (E-6051) |
| | IANBD-ester (I-9) |
| | Iodoacetamido-fluorescein (I-15) |
| ABD-N | BODIPY TMR cadaverine iodoacetamide (D-6012) |
| | ALEXA FLUOR 546 C-5 maleimide (A-10258) |
| BTCS or Elbaum's sulfonamide (similar emission spectra) | ALEXA FLUOR 532 C-5 maleimide (A-10255) |
| | Eosin-5-iodoacetamide (E-99) |

Dapoxyl sulfonamide binds to holoprotein tightly (Kd=0.2 μM) [31], exhibiting a twenty-fold increase in quantum yield and lifetime upon excitation at 365 nm, and approximately a 60 nm blue shift in its emission (FIG. 3). If the Dapoxyl is in the presence of holo-CA covalently labeled at a position close to the binding site with a fluorophore (such as ALEXA FLUOR 594) which absorbs well at wavelengths where bound Dapoxyl sulfonamide emits (about 550 nm), the Dapoxyl sulfonamide will bind to the protein and (being thus in close proximity) transfer its energy by the Förster mechanism to the label, which in turn emits at about 617 nm. Naturally, the efficiency of the energy transfer depends on the proximity of the label and Dapoxyl sulfonamide, their relative orientation, and their spectral overlap [37]. The introduction of cysteine residues into the protein structure at predetermined points by site directed mutagenesis permits the covalent label to be positioned optimally for energy transfer [38]. With excitation at 365 nm, the emission at 617 nm should be fairly strong, because although the ALEXA FLUOR absorbs poorly at this excitation wavelength, Dapoxyl absorbs well and transfers its energy to the ALEXA FLUOR which emits well at 617 nanometers. Exciting this mixture at 548 nm yields the strong fluorescence of the ALEXA FLUOR label only, since Dapoxyl does not absorb at this wavelength. The wavelengths 365 and 548 nm are mercury emission lines, and chosen for the convenient use of that excitation source; other wavelengths nearby will also work, although the numerical value of the ratio is changed somewhat. In the absence of Zn(II) the protein is in the apo-form, and the Dapoxyl sulfonamide does not bind; as a result its emission is weak, and there is no propensity to transfer energy to the ALEXA FLUOR 594 since on the average the Dapoxyl sulfonamide will be thousands of Angstroms away from the ALEXA FLUOR 594-labeled protein at micromolar concentrations, and energy transfer will be negligible. Thus in the absence of zinc the only emission expected at 617 nm with excitation at 365 nm will be the weak emission of the ALEXA FLUOR 594 (which absorbs poorly) and the weak emission of free Dapoxyl sulfonamide. With excitation in the green at 548 nm the emission at 617 nm is essentially unchanged, since one only excites the ALEXA FLUOR at this wavelength. Consequently, at low zinc concentrations we expect a low ratio of emission excited at 365 and observed at 617 nm to that excited at 548 nm and observed at 617 nm; whereas at higher zinc concentrations the ratio increases since the intensity excited at 365 nm and observed at 617 nm will increase.

We have made several variants of CA with cysteinyl residues replacing amino acid residues on the surface of the protein which are usable with the present invention; a particular variant's usability depends upon i) the proximity of the acceptor fluorophore conjugated to it to the fluorescent aryl sulfonamide donor, compared with the spectroscopically determined Forster distance of the donor; ii) the stability of the conjugate; and iii) the ease and yield of making the conjugate. The last two issues are typical in the conjugating of fluorescent compounds to proteins and are well known to the art. These variants (from all of which stable fluorescent conjugates have been made), together with the distance from the cysteinyl sulfur to the sulfonamido nitrogen in Angstroms include: L198C (<10), N67C (10), H64C (9), H36C (20), Y7C (10), S166C (22). Note that because of the inverse $R^6$ dependence of energy transfer and the overall small size of carbonic anhydrase, even middling spectral overlap results in high energy transfer efficiency; for instance a donor-acceptor distance of 20 Angstroms and a mediocre Forster distance of 30 Angstroms results in better than 90% efficiency, whereas the Forster distances of many of the pairs below are upwards of 40 Angstroms. Preferred variants include S166C, L198C and H36C, the first because the conjugation of the fluorophore is distant enough from the donor that there is no interference in the donor's binding.

The carbonic anhydrase-based FRET sensor has several advantages over other zinc indicators. First, the fact that it is ratiometric makes it less sensitive to many artifacts and easier to calibrate, unlike most other zinc probes [9, 11, 14]. Also, it is extremely selective due to the properties of the carbonic anhydrase zinc ion binding site [23]. It is more than ten thousand-fold more sensitive than the most selective ratiometric indicator (FuraZin-1), and at least five orders of magnitude more selective than the most sensitive ratiometric indicator (Fura-2) [10].

The method of the present invention has several advantages beyond those inherent in using excitation ratios. A key issue in quantitating free Zn(II) in cells using apo-CA and aryl sulfonamides are the unknown and potentially variable amounts of carbonic anhydrase likely to be found therein. In this case one only observes the emission from the ALEXA FLUOR 594-labeled protein, so Dapoxyl bound to CA in the cell does not contribute significantly. Although Dapoxyl sulfonamide exhibits fluorescence when bound to membranes that is comparable to that when bound to holocarbonic anhydrase [31], the fact that it is not in close proximity to the ALEXA FLUOR-labeled carbonic anhydrase II means that energy transfer is unlikely and no increase in ALEXA FLUOR emission should be observed. An important issue is how the quantitation of zinc is affected by the presence of varying amounts of Dapoxyl sulfonamide. However, in this case (except for the weak emission from the free Dapoxyl) again one is only observing the ALEXA FLUOR emission, and if excess Dapoxyl sulfonamide over ALEXA FLUOR-labeled CA is present, it will contribute only minimally. Of course, if either Dapoxyl sulfonamide or ALEXA FLUOR-labeled protein is present at concentrations significantly under the KD of 0.2 µM, the fractional saturation with the sulfonamide will be less than that of the zinc in the active site, and the zinc concentration will be underreported. Thus at intermediate concentrations at least the ratio is likely to be largely independent of the Dapoxyl sulfonamide concentration.

The biosensing approach of the invention thus has substantial potential for measuring very low levels of zinc in biological systems. The affinity of CA for zinc and its selectivity with respect to other metals can be tuned over a broad range by subtle modification of the carbonic anhydrase structure [23]. It is ideal for extracellular measurements. For intracellular determination the protein component can be introduced into a cell by any of several means known in the art, including but not limited to: microinjection, gene gun, lipid vesicle fusion, or introduction as a PEBBLE [43]. Most preferably, intracellular measurements of zinc can be performed using a fusion protein of CA and a Green Fluorescent Protein (GFP) or variant thereof.

Dapoxyl sulfonamide is rapidly cell-permeant and can be added to the medium used to culture the cells. It is preferred that the donor fluorophore used in the present invention have this property if intracellular measurement of zinc is to be performed. Many aryl sulfonamides are expected to be cell permeant.

As noted above, for measurement of zinc ion concentration in vivo, it is desirable to express a CA-fluorescent protein fusion protein within the cell. The fluorescent protein serves as the acceptor fluorophore and the zinc dependent CA-binding donor fluorophore should be added to the culture medium in a manner that provides for its permeation through the cell membrane. Such an embodiment of the invention can be used in situations in which it is not easy to get into a cell across the membrane, or easy to get into a particular cell or group of cells by microinjection, insertion using a lipid reagent, or other means. Miyawaki, et al, [Miyawaki (1997) Nature 388:882-887, hereby incorporated by reference] describe a protein-based fluorescent calcium indicator based on a fusion protein of Blue Fluorescent protein, Green fluorescent Protein, and calmodulin. When calmodulin binds Ca, it undergoes a dramatic conformational change which changes the distance or relative orientation (or both) between the two fluorescent protein molecules which changes the efficiency of energy transfer from the blue to the green. The concentration of calcium can thus be measured by the change in energy transfer efficiency which can be measured by several means well known to the art. The advantage of the Miyawaki approach is that the gene for the fusion protein can be inserted into many different kinds of cells and expressed therein by means well known in the art. Thus the indicator system, at least the protein part, is manufactured inside the cell of choice, instead of having to traverse the membrane.

This concept can be applied in the present invention by substituting a CA-fluorescent protein fusion protein for the CA-fluorescent dye conjugate. Such a fusion protein can be made by constructing a gene comprised of the gene for a CA variant attached to the gene for a suitable fluorescent protein such as Yellow Fluorescent Protein or DsRed. Vectors for production of fusion proteins with fluorescent proteins such as Green Fluorescent Protein, Yellow Fluorescent Protein, DsRed and the like are available commercially. For example pEGFP for expression of fusion proteins with EGFP in bacteria, pEGFP-C2 for expression of fusion proteins with EGFP in mammalian cells, and corresponding vectors for fusion to DsRed and other fluorescent proteins, are available from the Clontech division of Becton Dickenson. The gene for the fluorescent protein is fused to that for human CA II using molecular biology methods well known to the art. Vectors for targeting of the fusion protein to particular cell compartments, such as the nucleus, mitochondria or peroxisomes, are also available from Clontech/Becton Dickenson.

The fusion of the CA or selectively zinc-binding variant thereof with the fluorescent protein will preferably place the zinc-dependent sulfonamide binding site within 15 to 45 angstroms, preferably from 15 to 35 angstroms, more preferably from 15 to 25 angstroms, of the fluorophore site of the fluorescent protin. Sulfonamide binding sites on CA and zinc-binding variants thereof, and fluorophore sites of fluorescent proteins, especially of Green Fluorescent Proteins and variants thereof having altered spectral properties, are considered known in the art.

One can choose a fluorescent protein based on its spectral properties to provide a good overlap and thus accept energy from a given fluorescent sulfonamide. In this case one is limited to placing the fluorescent protein either at the N- or C-terminus of the CA, so it may be difficult to get as efficient transfer of energy from the fluorescent donor as can be achieved using the fluorescent conjugates described above. In the case of CA, the N- and C-termini are on the back of the molecule, nearly equidistant from the sulfonamide binding site, so it makes only a modest difference whether the fluorescent protein is fused to the N- or C-terminus. Listed below are fluorescent aryl sulfonamides paired with fluorescent proteins whose genes are commercially available for fusion to CA and whose spectral properties are satisfactory as acceptors:

| Sulfonamide | Fluorescent Protein |
| --- | --- |
| dansylamide | Enhanced Cyan Fluorescent Protein (ECFP) |
| ABD-N | DsRed |
| Dapoxyl sulfonamide | DsRed |
| | HcRed |
| BTCS or Elbaum's | Enhanced Yellow Fluorescent Protein (EYFP) |

In this embodiment, it is easy to get Dapoxyl sulfonamide or another relatively hydrophobic fluorescent sulfonamide to penetrate cells, so the measurement can be made anywhere the fusion protein can be expressed. The instant embodiment contemplates use of fluorescent, hydrophobic sulfonamides as preferred donor fluorophores.

In the event that the CA-fluorescent protein fusion is to be used in vitro, the protein can be purified by methods known in the art, e.g. by carbonic anhydrase affinity chromatography (P.L Whitney (1974), Anal. Biochem. 57:467-476, hereby incorporated by reference).

Others have made fluorescent protein fusions which when expressed exhibit fluorescence changes in response to changes in zinc concentration (L. L. Pearce et al. (2000), Proc. Natl. Acad. Sci, USA 97:477-482; K. K. Jensen et al. (2001), Biochemistry 40:938-945; both hereby incorporated by reference), but these workers do not teach a separate fluorescent ligand which binds to the fluorescent protein fusion in a metal-dependent fashion. In any case the sensitivity of these approaches is much worse (thousand to million-fold).

In vitro measurements of fluorescence intensity according to the invention can be performed using either fluorescence microscopes or fluorescence spectrometers well-known in the art. In vivo measurements of fluorescence intensity, especially in the instance where the sample is a living cell, are preferably made using a fluorescence microscope. Use of a microscope for the assay provides not only quantitation of the zinc ion, but also its location within the sample, e.g. in a particular cellular compartment. Thus, movement of zinc ion between compartments of a cell or within parts of a tissue slice can be effectively monitored.

EXAMPLE 1

Use of Purified CA to Quantitate Zinc Ion in vitro

Materials and Methods

The L198C variant of human apocarbonic anhydrase II was constructed, expressed in E. coli BL21 cells, and purified as previously described [39]. The protein was conjugated with ALEXA FLUOR 594 maleimide (Molecular Probes, Eugene, Oreg.) at the introduced cysteinyl residue and the zinc ion removed also as previously described [40]. Dapoxyl sulfonamide was synthesized as described [31], and further purified from the residual sulfonic acid form by silica gel column chromatography in chloroform:methanol 3:1; the purification may be assessed by monitoring the blue fluorescence of the acid form and the yellowish fluorescence of the sulfonamide under 365 nm excitation. Steady state fluorescence spectra were acquired on a Spectronics AB-2 fluorometer, and zinc ion buffers were formulated using the MINEQL program (Environmental Research Software, Hallowell, Me.).

Results

From the overlap of the emission spectrum of the Dapoxyl sulfonamide with the excitation spectrum of ALEXA FLUOR 594 FIG. 3, it is apparent that Förster transfer will occur from the former to the latter if they are brought into close proximity, and their dipoles are not rigid and orthogonal. In fact by attaching the ALEXA FLUOR at position 198, it should be quite close, less than 10 angstroms from the Dapoxyl sulfonamide if it binds in a manner similar to dansylamide [41]. Calculating the overlap integral from the spectra and assuming the fluorophores exhibit an orientation factor ($\kappa2=2/3$) indicates that the R0, the so-called Förster distance where transfer is 50% efficient, is 38 Angstroms, and that the transfer efficiency of the bound Dapoxyl sulfonamide to the ALEXA FLUOR should be greater than 99 percent. That the energy transfer depends on free zinc binding and not solely due to zinc-independent binding of the sulfonamide may be seen in FIG. 4, which depicts the emission spectra of fixed concentrations of ALEXA FLUOR 594-labeled apo L198C and Dapoxyl sulfonamide as a function of zinc concentration. The increase in intensity of the emission at 617 nm is due to energy transfer from the Dapoxyl, as may be seen from the increase in apparent ultraviolet absorbance in the excitation spectra FIG. 5. The ALEXA FLUOR emission does not change significantly with varying zinc concentration in the absence of Dapoxyl sulfonamide (results not shown). The emission at 560 nm also increases with zinc concentration, but not as much as in the absence of the Alexa-fluor label [31]. This behavior occurs if the energy transfer is not quantitative, and in fact the 2.5-fold enhancement observed (instead of twenty-fold) is greater than expected with the 99+% energy transfer efficiency anticipated above. Three potential explanations for this "leakage" of Dapoxyl sulfonamide emission include the presence of small amounts of unlabeled L198C carbonic anhydrase, distortion of the protein structure such that the donor and acceptor are farther away than suggested by the crystal structure, and unfavorable orientation of rigidly bound donor and acceptor moieties such that the orientation factor ($\kappa2$) is not 2/3. In fact the 2/3 approximation which is widely used presumes that either the donor or acceptor (or both) rotates rapidly on the timescale of the donor lifetime, which can be an unwarranted assumption. In any event, the leakage of the donor fluorophore emission does not affect the utility of the assay.

If the ratio of fluorescence intensity with emission at 617 nm and excitation at 365 nm to that with excitation at 548 nm is plotted as a function of free zinc concentration, one observes binding saturation at concentrations much above 100 pM FIG. 6. The free zinc concentrations were maintained at these low levels using zinc buffers. The dependence on free zinc in the picomolar range is as expected, based on the known affinity of apo-CA for zinc [42]. The saturating behavior at higher zinc concentrations and the very low free zinc concentrations at which the effects are observed clearly indicate that the zinc dependence is not a collisional process but a binding phenomenon. The best fit single site binding isotherm to the data in FIG. 6 is indicated by the line and yields an apparent KD of 56±8 pM. This is significantly higher than that of the wild type protein (1 pM), but such differing affinities of variant CA's have frequency been observed. The absolute value of the ratio is not large because of the strong emission of the ALEXA FLUOR when excited at 548 nm, where its extinction coefficient is approximately 31,400 $M^{-1}$ $cm^{-1}$ whereas the extinction coefficient of the Dapoxyl sulfonamide is approximately 25,000 $M^{-1}$ $cm^{-1}$ at 365 nm, and the excitation intensity is less as well. The ratio increases 60% upon binding of the zinc, which is a usable change. The exact value of the ratio in any case depends on the relative excitation strength at the two excitation wavelengths, and the wavelengths chosen, thus the calibration in FIG. 6 is instrument-specific. From FIG. 6, the detection limit is in the vicinity of 10 pM. These results demonstrate that free zinc ion can be quantitated by an excitation ratiometric approach at picomolar levels, and suggest that ratiometric images may be obtained through the microscope as well.

EXAMPLE 2

Use of Additional CA Variants To Quantitate Zinc Ion in vitro

Labeling of the CA II variants, S166C and H36C

Before conjugation all proteins were dialyzed overnight at 4° C. in 500 ml of dialysis buffer (50 mM HEPES, 40 mM $Na_2SO_4$, 10 μM, Zn, pH 7.5) in order to rid the protein of any unwanted substances left over from purification. The starting protein concentration is determined by the OD at 280 nm. A typical starting concentration is around 30 μM. The cysteine residues are reduced with 1 mM Dithiothreitol (DTT) for one hour at room temperature. In order to conjugate the fluorescent label to the introduced cysteine the left over DTT it is dialyzed in 500 ml of dialysis buffer for 2 hours at room temperature. A 5 molar excess of the fluorescent label ALEXA FLUOR 594 (Molecular Probes, Eugene, Oreg.) is added to the reduced protein and reacted for 1 to 2 hours at room temperature in the dark. The reaction is stopped by adding 10 molar excess of β-mercaptoethanol over ALEXA FLUOR 594 (AF594). After 15 minutes the protein is placed in 600 ml of 50 mM HEPES, 40 mM $(NH_4)_2SO_4$, 10 μM Zn, pH 7.5 and dialyzed overnight at 4° C. The dialysis buffer is changed 2-3 times or until the buffer is colorless. Concentration of the label and the protein is determined by the absorbance at 590 nm and 280 nm respectively.

Apoization Of The Labeled Variant

In order to remove zinc from the protein it is dialyzed for 2 hours at room temperature in 350 ml of 100 mM HEPES, 50 mM Dipicolinic acid (DPA), pH 7.5. The buffer is changed once and the protein undergoes another 2 hours of dialysis. After this time the protein is transferred to 600 ml of chelexed 0.01 M MOPS pH 7.0 and dialyzed overnight at 4° C. The buffer is changed 1 to 2 times depending on the presence of DPA (indicated by broadening of the 280 peak on the UV-vis spectrophotometer).

Experimental procedures

The labeled protein and dapoxyl were added to each zinc buffer (Table 1) and incubated at room temperature for at least one hour to allow the protein to reach equilibrium. The typical concentrations used in these experiments were 0.5 μM protein and 0.5 μM dapoxyl. The labeled proteins were tested on a Spectronics AB-2 fluorometer with excitation scans taken from 300 nm-600 nm and emission set at 618 nm. In order to get a calibration curve for the fluorescence microscope (Nikon Eclipse TE300 inverted fluorescence microscope) the same samples used on the fluorometer were added to a 1536 well plate (12 μL per well) and placed upside down on the microscope. Pictures were taken with excitation 543 nm and then changing the filter to 365 nm with the emission filter set at 618 nm. Fluorescent images of the wells were captured with a Sensicam CCD camera (The Cooke Corporation, Auburn Hills, Mich.) and using IPLab software (Scanalytics Inc., Fairfax, Va.). The images taken with excitation 365 nm were then divided by the images taken with excitation 543 nm. With the 1536 well plate two wells show up per image using the camera, so it is important not to move the plate at all and take the two pictures (changing the excitation filter) before moving on to the next two wells. This way the wells overlap completely and the ratio image will turn out fine. For each ratio image a circular region of interest (ROI) is placed in the center of the well and the average intensity is calculated. These averages are then plotted and fit with a binding isotherm. The wells are normalized and pseudo colored for visual comparison of the intensity ratio.

TABLE 1

Zinc buffers for experiments made with 0.01 M chelexed MOPS, 0.002 M NTA, and volumetric Zn standard solution at pH 7.0.

| [Zn], (M) Total | [Zn], (M) Free |
| --- | --- |
| Control | 0 |
| 1.00E−09 | 2.13E−15 |
| 5.00E−09 | 1.06E−14 |
| 1.00E−07 | 2.13E−13 |
| 2.50E−07 | 5.23E−12 |
| 5.00E−07 | 1.06E−12 |
| 2.00E−06 | 4.26E−12 |
| 5.00E−06 | 1.07E−11 |
| 2.50E−05 | 5.46E−11 |
| 5.00E−05 | 1.12E−10 |
| 2.00E−04 | 5.23E−10 |
| 5.00E−04 | 2.13E−09 |
| 7.50E−04 | 6.39E−09 |
| 9.00E−04 | 1.92E−08 |
| 9.60E−04 | 5.10E−08 |

Results

Figure 8:
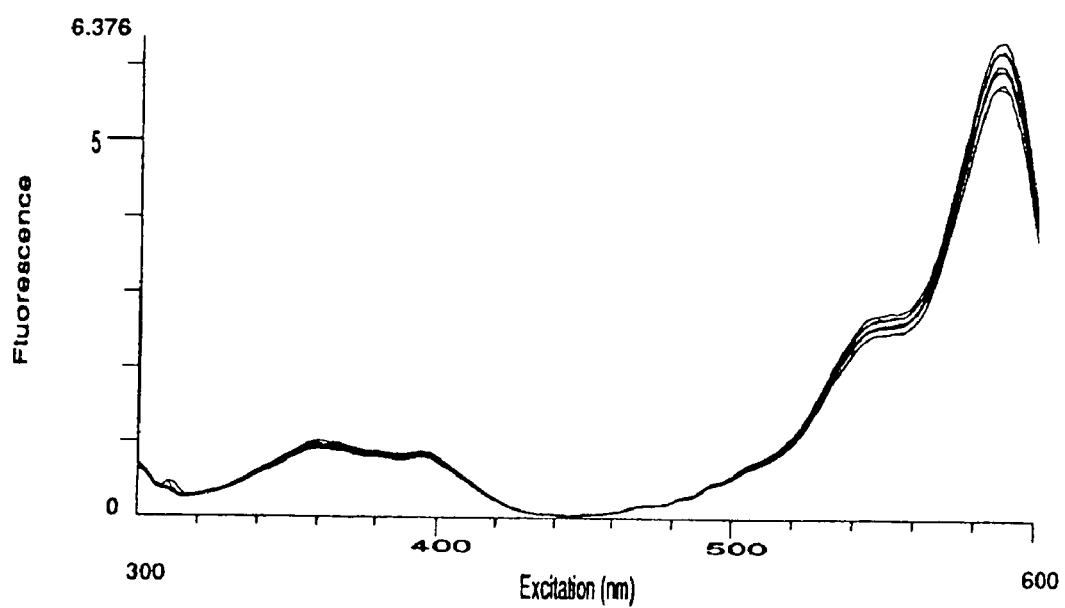
FIG. 8. Excitation scans of S166C-AF594 and dapoxyl sulfonamide in zinc buffers. This variant is also not showing any change in intensities at excitation 366 nm or 548 nm with increasing zinc concentration. Emission is set at 618 nm.

S166C-AF594 Conjugation of S166C with ALEXA FLUOR 594 resulted in a pink color not the dark purple color that was seen with L198C. The labeling efficiency of S166C is less than half that of L198C however the double peak close to the peak wavelength of AF594 was present (FIG. 7). Excitation scans with S166C-AF594 and dapoxyl sufonamide also resulted in minimal changes in fluorescence intensities with increasing zinc concentration using 0.5 μM S166C-AF594 and 0.5 μM dapoxyl (FIG. 8).

Figure 9:
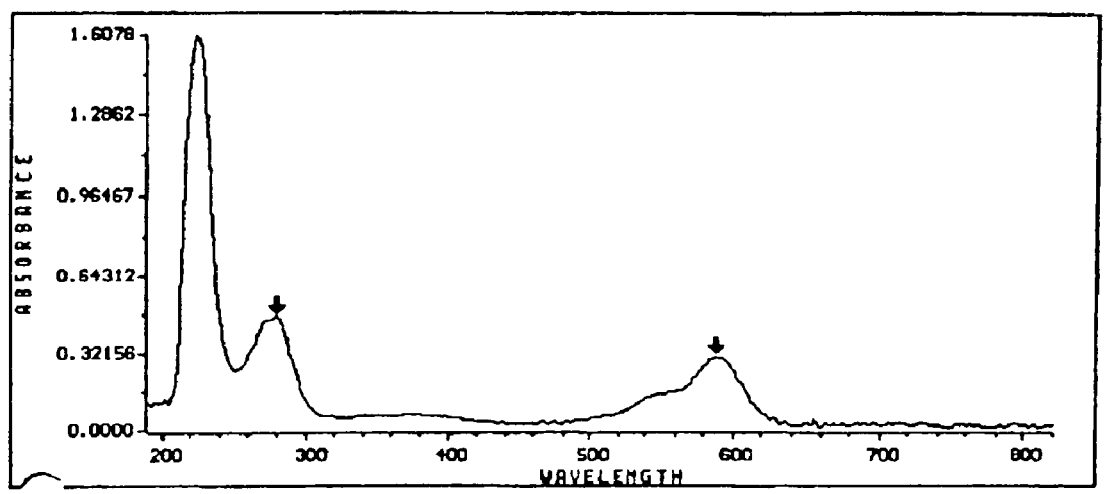
FIG. 9. UV-vis spectrum of apo-H36C-AF594 showing a good labeling ratio and the absence of the peak at 550 nm.
Figure 10:
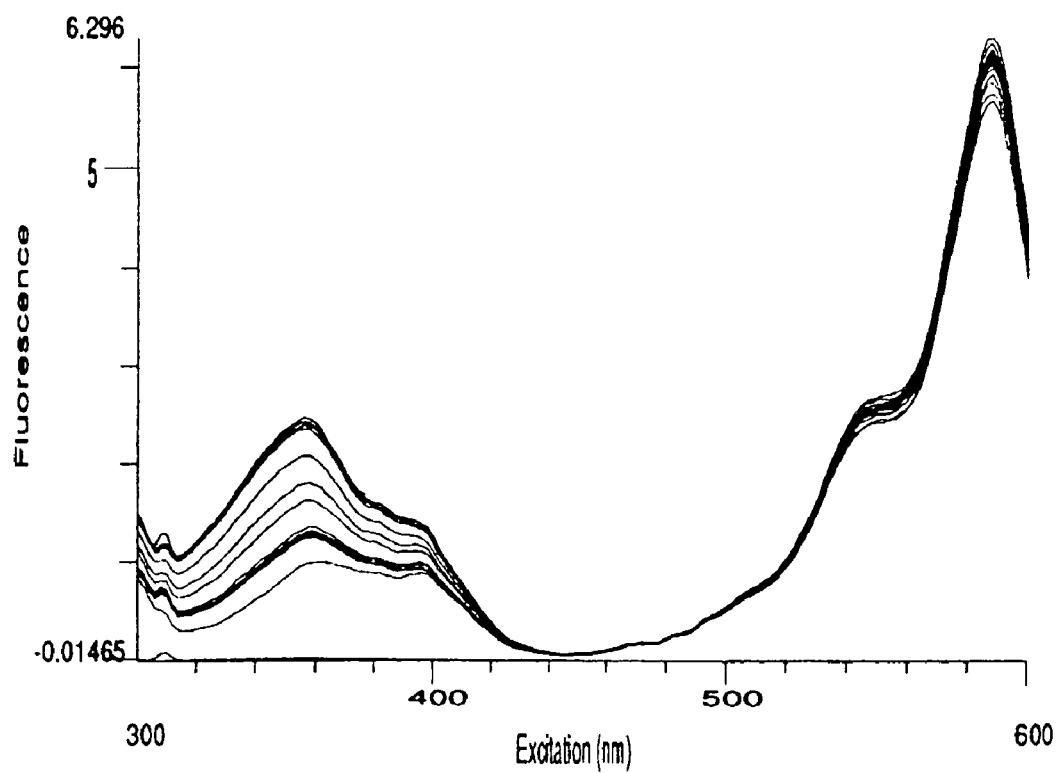
FIG. 10. Excitation spectra of apo-H36C-AF594 and dapoxyl sulfonamide in zinc buffers with emission 618 nm. There is a 50% increase in intensity at excitation 366 nm with increasing zinc concentration.
Figure 11:
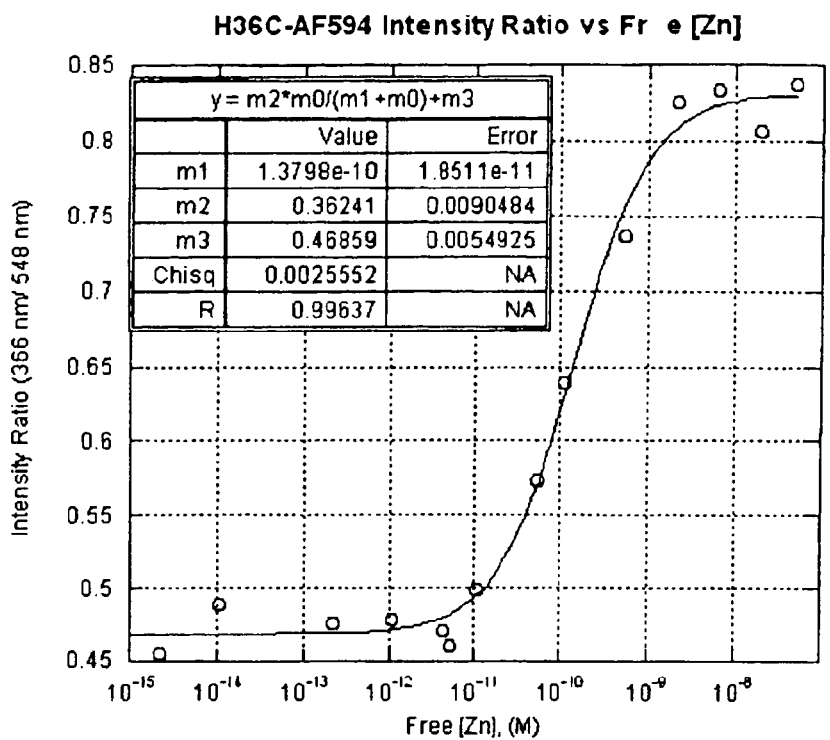
FIG. 11. Zinc dependent ratio of 366 nm over 548 nm with emission at 618 nm of apo-H36C-AF594 and dapoxyl sulfonamide.
Figure 12:
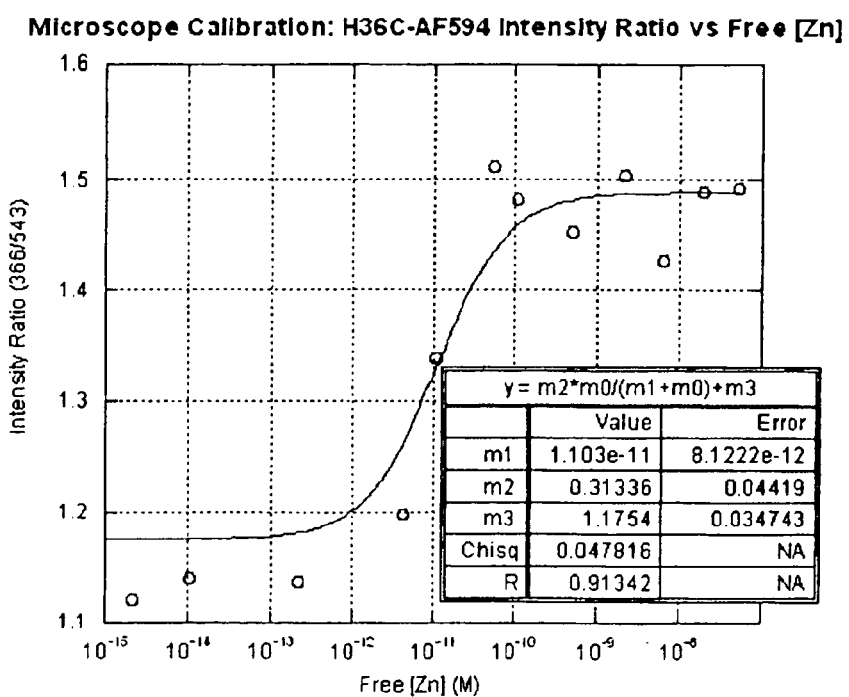
FIG. 12. Zinc dependent ratio of 366 nm over 548 nm with emission at 618 nm of apo-H36C-AF594 and dapoxyl sulfonamide in a 1536 well plate.
Figure 13:
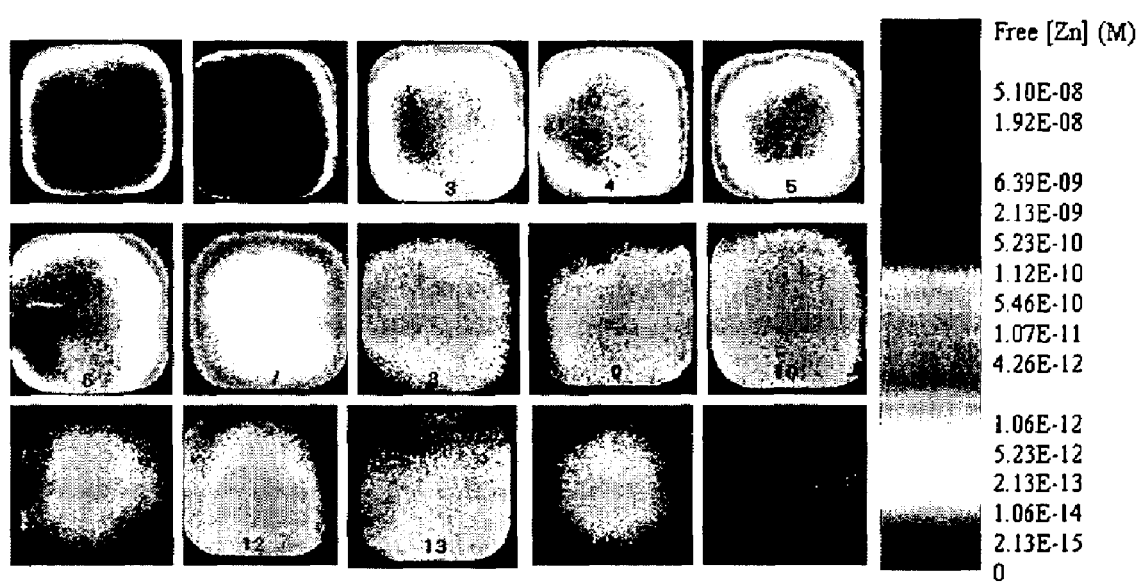
FIG. 13. Pseudo colored (rainbow) images printed in gray scale, of wells containing H36C-AF584 and dapoxyl sulfonamide in varying zinc concentrations (increasing from 1-15, shown left).

H36C-AF594 The labeling of H36C was comparable to that of N67C with a single peak at 590 nm (FIG. 9) and a nice pink color. Excitation scans showed almost a 50% increase in intensity at excitation 366 nm with only minimal changes at excitation 548 nm as the zinc concentration increases (FIG. 10). Plotting this data and fitting it to a binding isotherm reveals a detection limit around 10 pM (FIG. 11). Since this variant gave such a good response it was used for calibrating the fluorescence microscope. Images of the wells containing these samples were taken at excitation 543 nm and 365 nm. A ratio image of each well was created by dividing the two images (365/543). The mean intensity of each is calculated for an oval region of interest in the middle of the well, and this is the data used to calculate the calibration curve. Although the ratio range is higher than the one resulting from the AB-2, the data is still fit by a binding isotherm revealing a detection limit around pM or less (FIG. 12). A representative set of wells is used to create FIG. 13 in order to visually compare the intensity ratio of different zinc concentrations.

REFERENCES

The following articles of the scientific and patent literature are cited above. Each such article is hereby incorporated by reference in its entirety and for all purposes by such citation.

1. D. W. Choi and J. Y. Koh, "Zinc and brain injury," *Annu. Rev. Neurosci.* 21, 347-375 (1998).
2. C. J. Frederickson, S. W. Suh, D. Sulva, C. J. Frederickson, and R. B. Thompson, "Important of zinc in the central nervous system: the zinc-containing neuron," *J. Nutr.* 130, 1471S-1483S (2000).
3. J. H. Weiss, S. L. Sensi, and J. -y. Kah, "Zn(II): a novel ionic mediator of neural injury in brain disease," *Trends Pharmacol. Sci* 21, 395-401 (2000).
4. C. J. Frederickson and A. I. Bush, "Synaptically released zinc: Physiological functions and pathological effects," *BioMetals* (14, 353-366 (2001).
5. Y. Li, C. J. Hough, C. J. Frederickson, and J. M. Sarvey, "Induction of mossy fiber-CA3 long term potentiation requires translocation of synaptically released zinc," *J. Neurosci.* 21, S015-S025 (2001).
6. P. J. Fraker and W. G. Telford, "A reappraisal of the role of zinc in life and death decisions of cells," *Proc. Soc. Exp. Biol. Med.* 215, 229-236 (1997).
7. B. L. Vallee and K. H. Falchuk, "The biochemical basis of zinc physiology," *Physiol. Rev.* 73, 79-118 (1993).
8. J. M. Berg and Y. Shi, "The galvanation of biology: a growing appreciation for the rolex of zinc," *Science* 271, 1081-1085 (1996).
9. P. D. Zalewski, J. J. Forbes, and W. H. Betus, "Correlation of apoptosis with change in intracellular labile Zn(II) using Zinquin [(2-methyl-S-p-toluenesulphonamido-6-quinolyloxyacetic acid], a new specific fluorescent probe for Zn(II)," *Biochem. J.* 296, 403-408 (1993).
10. G. Grynkiewicz, M. Poenie, and R. Y. Tsien, "A new generation of calcium indicators with greatly improved fluorescence properties," *J. Biol. Chem.* 260, 3440-3450 (1985).
11. C. J. Frederickson, E. J. Kasarskis, D. Ringo, and R. F. Frederickson, "A quinoline fluorescence method for visualizing and assaying histochemically reactive zinc (bouton zinc) in the brain," *J. Neurosci. Methods* 20, 91-103 (1987).
12. T. Budde, A. Minta, J. A. White, and A. R. Kay, "Imaging free zinc in synaptic terminals in live hippocampal slices," *Neuroscience* 79, 347-358 (1997).
13. S. C. Burdette, G. K. Walkup, B. Spingler, R. Y. Tsien, and S. J. Lippard, "Fluorescent Sensors for Zn2+ based on a fluorescein platform: synthesis, properties, and intracellular distribution," *J. Am. Chem. Soc.* 123, 7831-7841 (2001).
14. G. K. Walkup, S. C. Burdette, S. J. Lippard, and R. Y. Tsien, "A new cell-permeable fluorescent probe for Zn2+, "*J. Am. Chem. Soc.* 122, 5644-5645 (2000).
15. T. Hirano, K. Kikuchu, Y. Urano, T. Higuchi, and T. Nagano, "Novel zinc fluorescent probes excitable with visible light for biological applications," *Angev. Chent. Int. Ed. Engl.* 39, 1052-1054 (2000).
16. E. Kimura and S. Aoki, "Chemistry of zinc(II) fluorophore sensors," *BioMetals* 14, 191-204 (2001).
17. P. Paoletti, P. Ascher, and J. Neyton, "High-affinity zinc inhibition of NMDA NR1-NR2A receptors,"*J. Neurosci.* 17, 5711-5725 (1997).
18. J. G. Reyes, "Zinc transport in mammalian cells," *Am. J. Physiol.* 270, C41-410 (1996).
19. C. E. Outten and T. V. O'Halloran, "Ferntomolar sensitivity of metalloregulatory proteins controlling zinc homeostasis," *Science* 292, 2488-2492 (2001).
20. Y. Li, C. Hough, S. W. Suh, J. M. Sarvey, and C. J. Frederickson, "Rapid translocation of Zn2+ from presynaptic terminals into postsynaptic hippocampal neurons after physiological stimulation," *J. Neurophysiol.* 86, 2597-2604 (2001).
21. S. Lindskog and P. O. Myman, "Metal-binding properties of human erythrocyte carbonic anhydrases," *Biochem. Biophys. Acta* 85. 462-474 (1964).
22. I. A. Hunt, M. Ahrued, and C. A. Fierke, "Metal binding specificity in carbonic anhydrase is influenced by conserved hydrophobic amino acids," *Biochemistry* 38, 9054-9060 (1999).
23. C. A. Fierke and R. B. Thompson, "Fluorescence-based biosensing of zinc using carbonic anhydrase," *BioMetals* 14, 205-222 (2001).
24. K. A. McCall, "Metal ion specificity and avidity in carbonic anhydrase variants," in *Department of Biochemistry*. Duke University, Durham, N.C. 190 pp. (2000).
25. R. B. Thompson, W. O. W. Jr. B. P. Maliwal, C. A. Fierke, and C. J. Frederickson, "Fluorescence microscopy of stimulated Zn(II) release from organotypic cultures of mammalian hippocampus using a carbonic anhydrase-based biosensor system," *J. Neurosci. Methods* 96, 35-45 (2000).
26. K. Listiak, S. W. Suh, B. Bell, J. Chen, D. Silva, M. Motamedi, G. Schneider, W. Whetsell, R. B. Thompson, and C. J. Frederickson, "Detection of pathological zinc accumulation in neurons: methods for autopsy, biopsy, and cultured tissue," *J. Histochem. Cytochem.* 47: 969-972 (1999).
27. S. Lindskog, L. E. Henderson, K. K. Kannan, A. Lijas, P. O. Nyman, and B. Strandberg, "Carbonic anhydrase," in *The Enzymes*, P. D. Boyer, Ed. Vol. 6, pp. 587-665, Academic, N.Y. (1971).
28. R. B. Thompson and E. R. Jones, "Enzyme-based fiber optic zinc biosensor," *Anal. Chem.* 65, 730-734 (1993).
29. D. Elbaum, S. K. Nair, M. W. Patchan, R. B. Thompson, and D. W. Christianson, "Structure-based design of a sulfonamide probe for fluorescence anisotropy detection of zinc with a carbonic anhydrase-based biosensor," *J. Am. Chem. Soc* 118, 3381-8387 (1996).
30. R. B. Thompson, B. P. Maliwai, and C. A. Fierke, "Expanded dynamic range of free zinc ion determination by fluorescence anisotropy," *Anal. Chem.* 70, 1749-1754 (1998).
31. R. B. Thompson, B. P. Maliwal, and H. H. Zeng, "Zinc biosensing with multiphoton excitation using carbonic anhydrase and improved fluorophores," *J. Biomed. Opt.* 5, 17-22 (2000).
32. M. vandeVen and E. Graton, "Time-resolved fluorescence lifetime imaging," in *Optical Microscopy: Emerging Methods and Applications*, B. Herman and J. J. Lemasters, Eds., pp. 373-403. Academic, N.Y. (1994).
33. H. Szmacinski, J. R. Lakowicz, and M. L. Johnson, "Fluorescence lifetime imaging microscopy: homodyne technique using high-speed gated image intensifier," in *Numerical Computer Methods. Methods in Enzymology*, M. L. Johnson and L. Brand, Eds., pp. 723-748, Academic, N.Y. (1994).
34. C. J. R. vanderOrd, C. J. deGrauw, and H. C. Gerritsen, "Fluorescence lifetime imaging module LIMO for confocal laser scanning microscopy," *SPIE Conf. on Advances in Fluorescence Sensing Technology V*, San Jose, Calif. (2001).
35. D. Axelrod, "Fluorescence polarization microscopy," *Methods in Cell Biology: Fluorescence Microscopy of Living Cells in Culture. Part B: Quantitative Fluorescence Microscopy-Imaging and Spectroscopy*, D. L. Taylor and Y, -L. Wang, Eds., Vol. 30, pp. 333-352, Academic, N.Y. (1989).
36. K. Fushimi, J. A. Dix, and A. S. Verkman, "Cell membrane fluidity in the intact kidney proximal tubule measured by orientation-independent fluorescence anisotropy imaging," *Biophys. J.* 57, 241-254 (1990).
37. T. Forster, "Intermolecular energy migration and fluorescence (Ger)," *Ann. Phys. (Leipzig)*, 2, 55-75 (1948).
38. R. B. Thompson, Z. Ge, M. W. Patchan, and C. A. Fierke, "Performance enhancement of fluorescence energy transfer-based biosensors by site-directed mutagenesis of the transducer," *J. Biomed. Opt.* 1, 131-137 (1996).
39. J. F. Krebs and C. A. Fierke, "Determination of catalyne activity and stability of carbonic anhydrase II as revealed by random mutagenesis," *J. Biol. Chem* 268, 948-954 (1993).
40. J. B. Hunt, Mj J. Rhee, and C. B. Storm, "A rapid and convenient preparation of apocarbonic anhydrase," *Anal. Biochem.* 79, 614-617 (1977).
41. S. K. Nair, D. Elbaum, and D. W. Christianson, "Unexpected binding mode of the sulfonamide fluorophore 5-dimethylamin-1-naphthalene sulfonamide to human carbonic anhydrase II: Implications for the development of a zinc biosensor," *J. Biol. Chem.* 271, 1003-1007 (1996).
42. J. A. Hunt and C. A. Fierke, "Selection of carbonic anhydrase variants displayed on phage: aromatic residues in zinc binding site enhance metal affinity and equilibration kinetics," *J. Biol. Chem.* 272, 20364-20372 (1997).
43. H. A. Clark, M. Hoyer, M. A. Philbert, and R. Kopelman, "Optical nanosensors for chemical analysis inside single living cells. I. Fabrication, characterization, and methods for intracellular delivery of PEBBLE sensors," *Anal. Chem.* 71, 4831-4836 (1999).

What is claimed is:

1. A method for quantitation of zinc ion in a sample comprising:
   i) disposing in said sample a donor fluorescent sulfonamide fluorophore and a carbonic anhydrase protein having conjugated thereto an acceptor fluorophore, wherein the binding of said donor fluorophore to the conjugated carbonic anhydrase is dependent upon the presence of zinc ion complexed to the conjugated carbonic anhydrase;
   ii) measuring the intensity of a fluorescence emission of the acceptor fluorophore upon excitation of the donor fluorophore at a first excitation wavelength;
   iii) measuring the intensity of a fluorescence emission of the acceptor fluorophore upon excitation of the acceptor fluorophore at a second excitation wavelength;
   iv) obtaining the ratio of the intensities measured in steps ii) and iii) and;
   v) relating the quantity of zinc ion in the sample to the ratio obtained in step iv).

2. The method of claim 1, in which the donor fluorophore is Dapoxyl sulfonamide.

3. The method of claim 1, in which the acceptor fluorophore is pyrano[3,2-g:5,6-g']diquinolin-13-ium,6-[2-carboxyl-4 (or 2-carboxyl-5) [carboxamido-N-pentyl-N'-maleimide]phenyl]-1,2,10,11-tetrahydro-1,2,2,10,10,11-hexamethyl-4,8-bis(sulfomethyl); inner salt.

4. The method of claim 1, in which the carbonic anhydrase is human carbonic anhydrase II having a cysteine residue substituted for serine residue 166 or having a cysteine residue substituted for histidine 36 and the acceptor fluorophore is conjugated to said cysteine residue.

5. The method of claim 3, in which the carbonic anhydrase is human carbonic anhydrase II having a cysteine residue substituted for serine residue 166 or having a cysteine residue substituted for histidine 36 and the acceptor fluorophore is conjugated to said cysteine residue.

6. The method of claim 1, in which the donor fluorophore is selected from the group consisting of dansylamide and ABDN.

7. The method of claim 6, in which the acceptor fluorophore is tetramethyl rhodamine maleimide.

8. The method of claim 1, in which the acceptor fluorophore is tetramethyl rhodamine maleimide.

9. A method for quantitation of zinc ion in a sample comprising:
   i) disposing in said sample a donor fluorescent sulfonamide fluorophore and a fusion protein comprising a carbonic anhydrase protein and a fluorescent protein acceptor fluorophore, wherein the binding of said donor fluorophore to the fusion protein is dependent upon the presence of zinc ion complexed to the carbonic anhydrase domain of the fusion protein;
   ii) measuring the intensity of a fluorescent emission of the acceptor fluorophore upon excitation of the donor fluorophore at a first excitation wavelength;
   iii) measuring the intensity of a fluorescence emission of the acceptor fluorophore upon excitation of the acceptor fluorophore at a second excitation wavelength;
   iv) obtaining the ratio of the intensities measured in steps ii) and iii) and;
   v) relating the quantity of zinc ion in the sample to the ratio obtained in step iv).

10. The method of claim 9, in which the fluorescent protein is Green Fluorescent Protein, Enhanced Green Fluorescent Protein, Yellow Fluorescent Protein, DsRed, or Blue Fluorescent Protein.

11. The method of claim 10, in which the donor fluorophore is selected from the group consisting of dansylamide and ABDN.

12. The method of claim 10, in which the donor fluorophore is Dapoxyl sulfonamide.

13. The method of claim 9, in which the sample comprises a living cell.

14. The method of claim 9, in which the donor fluorophore is selected from the group consisting of dansylamide and ABDN.

* * * * *

UNITED STATES PATENT AND TRADEMARK OFFICE
CERTIFICATE OF CORRECTION

PATENT NO. : 7,491,545 B2
APPLICATION NO. : 10/673409
DATED : February 17, 2009
INVENTOR(S) : Richard Thompson et al.

Page 1 of 1

It is certified that error appears in the above-identified patent and that said Letters Patent is hereby corrected as shown below:

In the specification,

Column 1, line 4, after the title, insert the following paragraphs:

--GOVERNMENT RIGHTS IN THE INVENTION

"This invention was made with government support under Grant Number NS038585 awarded by the National Institutes of Health and Grant Number N00014-00-1-0921 awarded by the Office of Naval Research. The government has certain rights in the invention."

BENEFIT OF PROVISIONAL APPLICATION--

Signed and Sealed this
Tenth Day of May, 2016

Michelle K. Lee
*Director of the United States Patent and Trademark Office*